United States Patent
Richards et al.

(10) Patent No.: US 11,141,541 B2
(45) Date of Patent: Oct. 12, 2021

(54) EVENT CAPTURE DEVICE FOR MEDICATION DELIVERY INSTRUMENTS

(71) Applicant: Becton, Dickinson and Company, Franklin Lakes, NJ (US)

(72) Inventors: Andrew Richards, Durham, NC (US); Sean Ulrich, Raleigh, NC (US); Mircea Stefan Despa, Cary, NC (US); Sundeep Kankanala, Bloomington, IN (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 363 days.

(21) Appl. No.: 15/838,024

(22) Filed: Dec. 11, 2017

(65) Prior Publication Data

US 2018/0161513 A1 Jun. 14, 2018

Related U.S. Application Data

(60) Provisional application No. 62/433,725, filed on Dec. 13, 2016.

(51) Int. Cl.
*A61M 5/32* (2006.01)
*A61J 7/04* (2006.01)
*A61M 5/31* (2006.01)

(52) U.S. Cl.
CPC .......... *A61M 5/3202* (2013.01); *A61J 7/0418* (2015.05); *A61M 2005/3126* (2013.01); *A61M 2205/14* (2013.01); *A61M 2205/3317* (2013.01); *A61M 2205/3368* (2013.01); *A61M 2205/3379* (2013.01); *A61M 2205/3561* (2013.01); *A61M 2205/3584* (2013.01);
(Continued)

(58) Field of Classification Search
CPC ............ A61M 5/3202; A61M 2205/14; A61M 2209/08; A61M 2209/084; A61M 2209/086; A61M 5/31566; A61M 2005/3126; G08B 21/24; G06F 19/3462; G16H 20/12; G16H 20/17; G16H 20/10; A61J 7/0418; A61J 7/0427; A61J 7/0436; A61J 1/1412
See application file for complete search history.

(56) References Cited

U.S. PATENT DOCUMENTS 4,837,719 A * 6/1989 McIntosh .............. A61J 7/0481
702/177
6,294,999 B1 * 9/2001 Yarin .................... A61J 7/0481
340/573.1
(Continued)

FOREIGN PATENT DOCUMENTS

WO  WO 2016/118736   7/2016

OTHER PUBLICATIONS

International Search Report and Written Opinion dated Mar. 19, 2018 for PCT/US2017/065626, filed Dec. 11, 2017.

*Primary Examiner* — Nilay J Shah
(74) *Attorney, Agent, or Firm* — Knobbe Martens Olson & Bear, LLP

(57) ABSTRACT

Described herein is a dose monitoring device configured to couple with one or more medication delivery instruments to capture, record and/or process dosing events or events of delivering a medication dose. The dose monitoring device may include electronics such as a sensor, a clock module and a temperature module related to monitoring the time of dosing events.

22 Claims, 6 Drawing Sheets

(52) U.S. Cl.
CPC . *A61M 2205/3592* (2013.01); *A61M 2205/50* (2013.01); *A61M 2205/502* (2013.01); *A61M 2205/52* (2013.01); *A61M 2205/581* (2013.01); *A61M 2205/587* (2013.01)

(56) References Cited

U.S. PATENT DOCUMENTS

| | | | |
|---|---|---|---|
| 6,302,855 B1* | 10/2001 | Lav | A61B 5/14532 600/584 |
| 9,250,111 B2* | 2/2016 | Whalley | A61M 5/31 |
| 2003/0099158 A1* | 5/2003 | De la Huerga | A61J 7/0084 368/10 |
| 2011/0295215 A1* | 12/2011 | Nielsen | G16H 20/17 604/257 |
| 2014/0018733 A1* | 1/2014 | Sjolund | A61J 7/0472 604/111 |
| 2014/0200545 A1* | 7/2014 | Bengtsson | A61M 5/24 604/506 |
| 2014/0207080 A1* | 7/2014 | Allerdings | A61M 5/31525 604/207 |
| 2014/0266760 A1* | 9/2014 | Burke, Jr. | G06F 19/3462 340/687 |
| 2014/0371682 A1* | 12/2014 | Bengtsson | G06F 19/3468 604/189 |
| 2016/0213853 A1* | 7/2016 | Despa | A61M 5/31548 |
| 2016/0324726 A1* | 11/2016 | Roberts | A61J 7/02 |
| 2019/0001067 A1* | 1/2019 | Berey | A61M 5/003 |

* cited by examiner

EVENT CAPTURE DEVICE FOR MEDICATION DELIVERY INSTRUMENTS

RELATED U.S. APPLICATIONS

This application claims priority to U.S. Provisional Appl. No. 62/433,725 filed on Dec. 13, 2016, which is hereby incorporated by reference in its entirety.

BACKGROUND

Field

The invention relates to medication delivery instruments, and more particularly, relates to smart devices for capturing events from medication delivery instruments.

Description of the Related Art

There are multiple diseases wherein patients have an active role in disease management. Under some treatment regimens, a patient may be required to dose medicament multiple times per day. For example, patients may take pills several times per day according to their prescriptions. In another example, diabetic patients may self-inject insulin in order to control blood sugar levels. When preparing to administer or self-inject medicament, a patient may need to take several factors into account. For example, a patient may need to keep track of the precise times at which previous doses were administered in order to calculate the dose time for a subsequent self-injection. It can prove difficult for a patient to accurately record and keep track of every dose time, particularly when many doses are delivered in a single day. This issue creates a possibility the patient miscalculating the dosing times for subsequent self-injections.

In order to remedy the issue, others have focused on sensors configured to passively or actively record dosing events. For example, Timesulin™ and InsulCheck™ are devices specifically designed for an insulin pen and can passively record an event when the respective device is removed from and replaced onto the insulin pen. The elapsed time since the last injection may be displayed to the user on a LCD display. However, these devices do not transmit data to other external devices and do not allow for user interaction. These devices also cannot be used for a multitude of different medication delivery instruments.

Vigilant Bee™ replaces an existing insulin pen cap and actively records user interactions such as twisting a dial and pressing a button on the device. The user interaction events are then transmitted to a smartphone via Bluetooth Low Energy. Vigilant Bee™ is used to record insulin dose time, insulin dose volume and blood glucose level. The device also contains an LCD display. However, as with other devices, the Vigilant Bee device cannot be used for a multitude of different medication delivery instruments.

In a non-medical context, Flic™ and PebbleBee Stone™ are configurable Bluetooth Low Energy buttons. Each device has a single button that the user may press. The button press event is transmitted to a companion smartphone app, which then performs one or more pre-configured actions such as turning on/off a WiFi light bulb. Flic™ and PebbleBee Stones™ are not designed for medical products, and the companion smartphone app of the devices does not support medical products.

SUMMARY

An embodiment may be a dose monitoring device configured to couple with one or more medication delivery instruments, comprising: a housing configured to mate with a medication delivery instrument; one or more position sensors configured to detect the presence or absence of the medication delivery instrument; a first environmental sensor configured to detect one or more environmental events; a clock module configured to record the time when the housing detects the presence or absence of the medication delivery instrument; and a communication module configured to transmit data from the position sensors or environmental sensors to an external device.

In one aspect of the embodiment, the medication delivery instrument may be an insulin pen, syringe, or vial. The medication delivery instrument may be an insulin pen, and the dose monitoring device may comprise a replacement cap configured to mate with the insulin pen. In another aspect of the embodiment, the one or more sensors may comprise a switch, a dial or a button. In yet another aspect of the embodiment, the external device may comprise a cellular telephone or network server.

In one aspect of the embodiment, the dose monitoring device may further comprise a temperature sensor configured to measure ambient temperature. In another aspect of the embodiment, the dose monitoring device may further comprise one or more indicators configured to display data from the one or more position sensors. In yet another aspect of the embodiment, the dose monitoring device may further comprise a processor configured to determine one or more future dosing events based on data from the one or more sensors or the clock module. The does monitoring device may further comprise one or more indicators configured to exhibit the one or more future dosing events. In one aspect of the embodiment, the dose monitoring device may further comprise a receiver module configured to receive information from the external device.

Another embodiment may be a method for recording dosing events with a dose monitoring device, comprising: providing a medication delivery instrument; detecting engagement of the dose monitoring device with the medication delivery instrument, wherein the dose monitoring device comprises: one or more position sensors; a clock module configured to record the engagement time; and a transmitter for transmitting data to an external device.

In one aspect of the embodiment, the one or more sensors may be configured to detect one or more dosing events or one or more user interactions with the dose monitoring device or the one or more medication delivery instruments. In another aspect of the embodiment, the one or more sensors may comprise a switch, a dial or a button. In yet another aspect of the embodiment, the medication delivery instrument may be an injectable medication delivery instrument such as an insulin pen or syringe. In yet another aspect of the embodiment, the medication delivery instrument may be a non-injectable medication delivery instrument, such as a pill box or insulin vial. In yet another aspect of the embodiment, the medication delivery instrument may be selected from a group consisting of an insulin pen, syringe, pill box, and insulin vial. The medication delivery instrument may be an insulin pen, and the dose monitoring device may be a replacement cap.

In one aspect of the embodiment, the method may further comprise displaying data from the one or more sensors or the clock module on a user interface. The data may comprise timestamps of one or more previous dosing events. In another aspect of the embodiment, the method may further comprise transmitting the data to an external device.

Any feature, structure or step disclosed herein can be replaced with or combined with any other feature, structure or step disclosed herein, or omitted. Further, for purposes of summarizing the disclosure, certain aspects, advantages and features have been described herein. It is to be understood that not necessarily any or all such advantages are achieved in accordance with any particular embodiment disclosed herein. No individual aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

Figure 1:
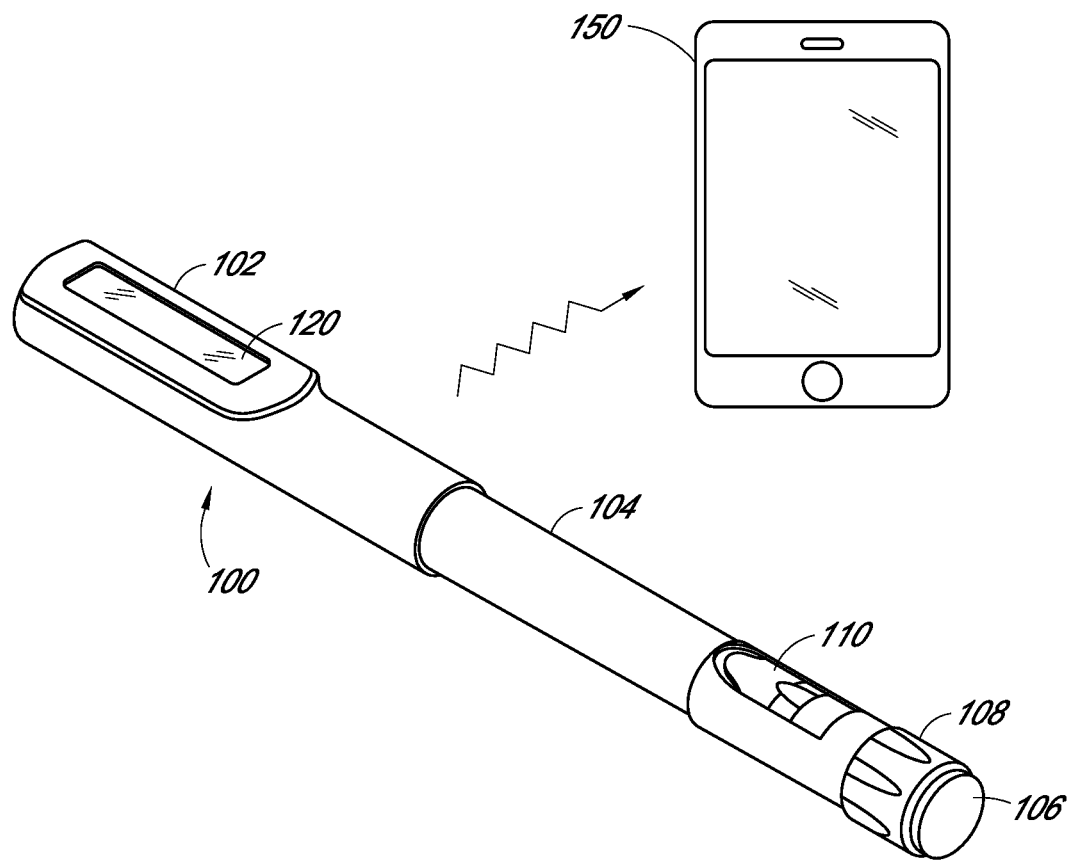
FIG. 1 depicts a dose monitoring device configured to couple with a medication delivery instrument and transmit data to an external device in accordance with an illustrative embodiment.

As will be appreciated by one skilled in the art, there are numerous ways of carrying out the examples, improvements and arrangements of a medicament delivery device in accordance with embodiments disclosed herein. Although reference will be made to the illustrative embodiments depicted in the drawings and the following description, these embodiments are not meant to be exhaustive of the various alternative designs and embodiments. Those skilled in the art will readily appreciate that various modifications may be made, and various combinations can be made, without departing from the embodiments discussed below.

Embodiments relate to a dose monitoring device configured to couple with one or more medication delivery instruments to capture, record and/or process medication dosing events. For example, the dose monitoring device may be a replacement cap that fits onto the medication delivery instrument. In one embodiment, the replacement cap fits over a conventional insulin pen and includes electronics to detect events such as the removal and reinstallation of the cap onto the insulin pen.

In one embodiment, the dose monitoring device records discrete data events that occur on the medication delivery instrument and use that data to capture one or more dose events. The dose monitoring device may capture or record non-medication dosing data, such as a timestamp or a temperature. The dose monitoring device may comprise a timer, a temperature or a sensor configured to measure environmental, or other, external information. In one embodiment, the dose monitoring device may be configured to couple with more than one medication delivery instruments.

In an illustrative embodiment, the dose monitoring device may be shaped to couple with one or more medication delivery instruments. In some embodiments, the dose monitoring device is shaped so that it can be attached and detached from more than one type or shape of medication delivery instruments.

The dose monitoring device may further comprise one or more connectors configured to physically couple the dose monitoring device with the one or more medication delivery instruments, either permanently or temporarily. The one or more connectors may be shaped to couple with the one or more medication delivery instruments. The one or more connectors may comprise clips, adhesive or hook-and-loop fasteners. In another embodiment, the dose monitoring device may be a primary module with a detachable or replaceable base. In this manner, the primary portion of the dose monitoring device may be the same regardless of the medication delivery instruments, but a detachable or replaceable base specific to a certain medication delivery instrument may be designed to promote better attachment and design aesthetics.

In an alternative embodiment, the dose monitoring device may not be physically coupled to the one or more medication delivery instruments, such as a key chain fob with a button.

In one aspect, the dose monitoring device may comprise one or more sensors configured to detect one or more dosing events or one or more user interactions with the dose monitoring device or the medication delivery instruments. The sensors may comprise a switch, a dial, a button or similar sensor. Multiple methods exist to capture dose events, and the methods may be classified as either active or passive. Active event detection requires user interaction and can be achieved using any number of user input forms such as a mechanical button or a capacitive button. An example of active event detection may include a dial or a button that the user operates when medication is taken from a pill box or when the dose monitoring device is used. Passive event detection does not require an active input from the user and can be achieved using any number of sensors. The sensors for passive event detection may be contact or non-contact based. The sensors for passive event detection may be mechanical, capacitive, optical or any combinations thereof. An example of passive event detection may include 1) a switch that is triggered during the use of the dose monitoring device or 2) a switch detecting when a pill box compartment is opened. The dose monitoring device may use active event detection, passive event detection or both. In one embodiment, the dose monitoring device may capture a single event at a time.

According to another embodiment, the dose monitoring device may be a battery-powered electronic button, or switch, that attaches to an existing medication delivery instrument. The user may press the button to indicate when a dose event has occurred. The button may transmit information wirelessly using Bluetooth, WIFI or another wireless transmission mechanism. The dose monitoring device may comprise additional input mechanisms such as extra buttons or dials in addition to the primary dose event capture mechanism. The dose monitoring device may further comprise a clock module configured to record one or more timestamps of when a button was pressed, or a switch was activated.

The medication delivery instruments may comprise injectable medication delivery instruments, such as insulin pens or syringes, or non-injectable medication delivery instruments, such as pill boxes or insulin vials. In another embodiment, the medication delivery instruments may be an insulin pen, and the dose monitoring device may be a replacement cap for the insulin pen. The replacement cap may comprise one or more electronic or software modules programmed to capture the dose event. The replacement cap may detect discrete events resulting from a patient removing and replacing the cap from the pen body. The cap may be programmed to record each such event, along with a timestamp of when the event occurred.

The user may attach the dose monitoring device to a medication delivery instrument prior to performing a dose event. For example, a diabetic patient may attach a replacement cap to an insulin pen in advance of performing an insulin injection. The user may either power up the dose monitoring device, or the dose monitoring device would automatically power up upon being coupled with the medication delivery instrument.

During an insulin administration procedure, the dose monitoring device replacement cap is first removed ("cap off" event); insulin is delivered to the user by injection; and the cap is replaced onto the insulin pen body ("cap on" event). In this embodiment, the dose event is indirectly inferred using a combination of passively captured "cap off" and "cap on" events and associated timestamps.

According to one aspect, the dose monitoring device may further comprise a processor connected to the one or more sensors and programmed to execute instructions configured to process data collected by the sensor and/or transmit the data to an external device. For example, that data captured for a dosing event may be used to determine the validity of the dosing event. In another example, the system may process dosing events and reject accidental button triggers or detections from a single modality. In another embodiment, dosing events may be combined with other data known about the patient, such as expected dose schedule, glucose levels and time of day, and analyzed by the system to facilitate better medication adherence with existing medication delivery instruments. For example, the system may review the dosing data to determine if the cap events occurred in a manner consistent with the user normal dosing of insulin. The instructions for carrying out this analysis may reside in a companion software application on a smartphone. In yet another embodiment, the instructions may be implemented in the dose monitoring device itself or on a server computer connected through a wide area network, such as the Internet.

In an illustrative embodiment, the dose monitoring device may further comprise one or more communication modules configured to transmit data to and/or receive data from an external device, such as a computer or a mobile device. The communication module may be connected to an external device using wired or wireless communication. The one or more communication modules may be configured to allow for connectivity between the dose monitoring device and one or more external devices. This connection may be made using well-known wireless communication protocols, such as Bluetooth, WiFi or other means. In another embodiment, the communication module can be configured to perform short-distance RF communication, such as Bluetooth, BLE, or ZigBee®. The dose monitoring device may further comprise one or more ports or slots to allow for a wired connection between the dose monitoring device and the external device. The transmitted data or information may be used to monitor or promote adherence to a medication regimen.

Furthermore, the dose monitoring device may comprise a data storage device such as a flash drive or memory card, or may be configured to engage such a data storage device in order to transmit data to or receive data from an external device. The dose monitoring device may further include a battery or a low power electronic module to provide power to the electronic components of the dose monitoring device.

The external device may be configured to conduct additional analysis, process or action on the transmitted data or information. For example, the external device may process dosing events to determine their validity. In another example, the external device may process dosing events and reject accidental button triggers or detections from a single modality. The time associated with one or more dosing events may then be recorded and displayed to the user on a user interface of the external device.

In one embodiment, the external device may maintain a timestamped log of captured dosing events. In another embodiment, the external device may alert the user if an event was not detected at a predefined time. The data or information may also be transmitted to a central server in a wide area network and distributed such that the data or information may be relevant and useful for a care provider to maintain patient adherence. The external device may also communicate information back to the dose monitoring device, such as for alerts or indications.

In one aspect, the dose monitoring device may further comprise one or more indicators to communicate data or information to the user. The indicators may comprise a visible LED, an audible buzzer, a display screen or any other user interface known in the art. The indicators may be configured to allow the user to access data recorded by the dose monitoring device. The user may access this data to determine time for the next injection. The indication may originate from the dose monitoring device itself or from off the device, such as from a companion smartphone app to the dose monitoring device. In another aspect, the dose monitoring device may further comprise a screen configured to display data or information to the user such as time since the last event and time until a scheduled event. The screen may comprise a LCD screen, an OLED screen, a touch screen, or any other screen known in the art.

Although various persons, including, but not limited to, a patient or a healthcare professional, can operate or use illustrative embodiments, for brevity an operator, patient or user will be referred to as a "user" hereinafter.

FIG. 1 depicts a schematic view of an illustrative embodiment of a dose monitoring device, or cap 102 coupled to an insulin pen body 104. The cap 102 is configured to transmit data to a smart phone 150. In this embodiment, a dose monitoring assembly 100 comprises the insulin pen body 104 and the cap 102. The cap 102 is configured to replace an existing cap for the insulin pen body 104.

The insulin pen body 104 comprises an injection button 106, a dosage selector 108 and a dose window 110. The dosage selector 108 comprises a dial which a user can operate to select the proper amount of insulin to administer in the next dose. The dose window 110 shows the dosage amount selected by the user. Once the user selects the dosage amount, the user may inject himself/herself with insulin from a needle within the insulin pen body 104 by operating the injection button 106.

The replacement cap 102 functions as a dose monitoring device and detects discrete events of removing and replacing the cap 102 from the pen body 104 and records the events along with timestamps. The replacement cap 102 comprises an indicator window 120 configured to display data, information or various state information to the user. The indicator 120 may be an electronic display configured to show the user the time data recorded by the replacement cap 102. The replacement cap 102 is shown as connected to a smartphone 150 via a wireless link. The wireless link may be any conventional wireless data link, including a Bluetooth Low Energy data link. The events of removing and replacing the replacement cap 102 from the pen body 104 are transmitted to the smartphone 150 and then read by a smartphone app in order to analyze or to assist the patient in monitoring adherence to a predetermined medication plan.

Figure 2:
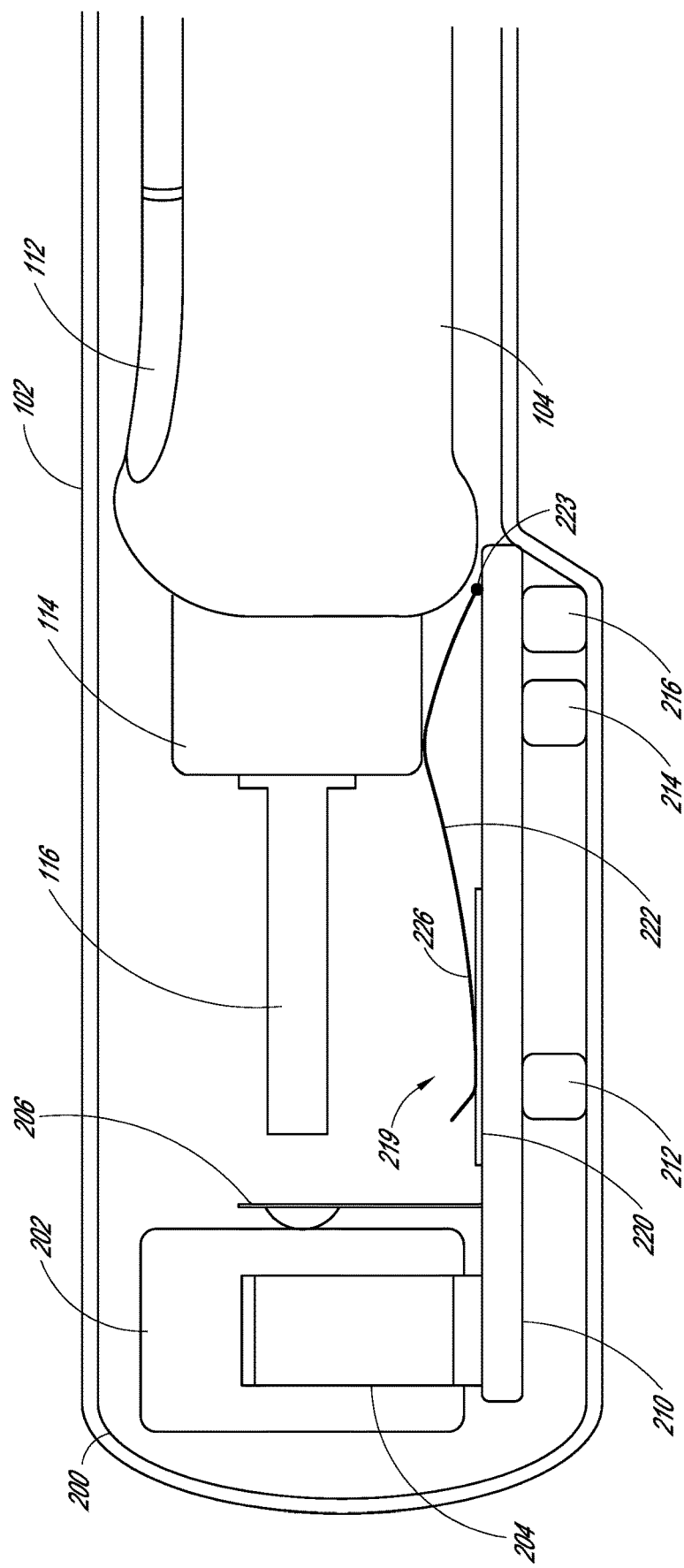
FIG. 2 depicts a cross-sectional side view of a dose monitoring device coupled to a medication delivery instrument in accordance with an illustrative embodiment.

FIG. 2 depicts a cross-sectional side view of the dose monitoring device cap 102 coupled to the insulin pen body 104. As shown in FIG. 2, the insulin pen body 104 further comprises an insulin reservoir window 112, which shows how much insulin is left in an insulin reservoir of the pen body 104. The distal end 114 of the insulin pen body 104 connects between a pen needle (not shown in FIG. 2) and the insulin pen body 104. Also shown is a needle cap 116, which protects the pen needle when the needle cap 116 is placed onto the distal end 114 of the pen body 104.

The replacement cap 102 also includes electronics configured to capture the dose events. As shown, the replacement cap 102 comprises an outer housing 200 which is designed to mate with the insulin pen body 104. The outer housing 200 has an internal chamber that includes an electronic module 202 that is electrically connected to a circuit board 210. The electronic module 202 is supported on the electronic board 210 by a support 204. A needle protector 206 is attached to the electronic module 202, or the electronic board 210, and protects the electronic module 202 from impacting the needle of the insulin pen body 104.

The electronic board 210 is supported by bases 212, 214, 216 and is electronically connected to the electronic module 202. The replacement cap 102 further comprises a switch 219, which detects the presence or absence of a distal end 114 of the pen body 104. The switch 219 comprises a switch plate 220 and a switch strip 222. The switch plate 220 is on top of the electronic board 210 and may be made of an electrically conductive metal material. The switch strip 222 may also be made of a conductive metal. A proximal end 223 of the switch strip 222 is connected to the electronic board 210, and the distal end 226 of the switch strip 222 does not contact the switch plate 220 in its natural biased state (i.e., when the switch strip 222 does not engage with the pen body 104). However, as shown in FIG. 2, when the cap 102 is engaged with the pen body 104, the distal end 114 of the pen body 104 presses on the switch strip 222 to cause it to make an electrical connection with the switch plate 220.

During an insulin administration procedure, the replacement cap is first removed ("cap off" event); insulin is delivered to a user by injection; and the cap is replaced onto the insulin pen body ("cap on" event). When the replacement cap 102 is replaced onto the insulin pen body 104 (i.e., "cap on" event), the distal end 114 of the insulin pen body 104 contacts and engages the switch strip 222 such that the distal end of the switch strip 222 contacts the switch plate 220 on the electronic board 210. The contact between the switch strip 222 and the switch plate 220 may close an electronic circuit, which is electronically communicated to the electronic module 202 to notify the electronics that the pen body 104 has been inserted into the replacement cap 102.

Figure 3:
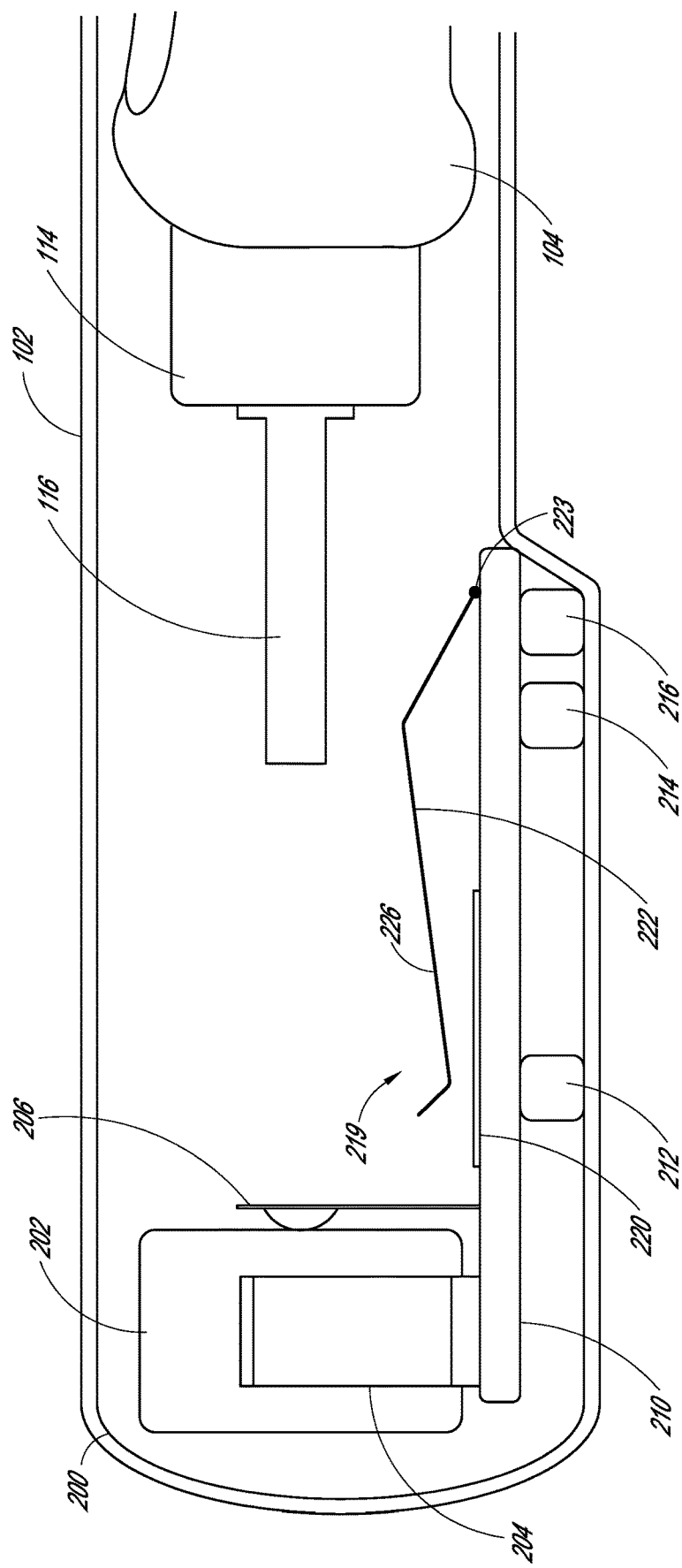
FIG. 3 depicts a cross-sectional side view of a dose monitoring device detached from a medication delivery instrument in accordance with an illustrative embodiment.

FIG. 3 depicts a cross-sectional side view of an illustrative embodiment of the insulin pen 104 detached as it is being withdrawn and disengaged with the pen cap 102. When the replacement cap 102 is removed from the insulin pen body 104 (i.e., "cap off" event), the distal end 114 of the insulin pen body 104 releases the switch strip 222 such that the distal end of the switch strip 222 does not contact the switch plate 220 on the electronic board 210. This breaks the electronic circuit closed by the contact between the switch strip 222 and the switch plate 220. The circuit break event is electronically communicated to the electronic module 202 to notify the removal of the distal end of the pen body 104 from the replacement cap 102.

Of course, it should be realized that any type of electronic switch that detects the insertion and withdrawal of the pen 104 is within the scope of embodiments described herein. For example, a button, slide switch, pressure switch, motion detector, or any other sensor for determining engagement of the pen 104 within the cap 102 is within the scope of the present embodiments.

Figure 4:
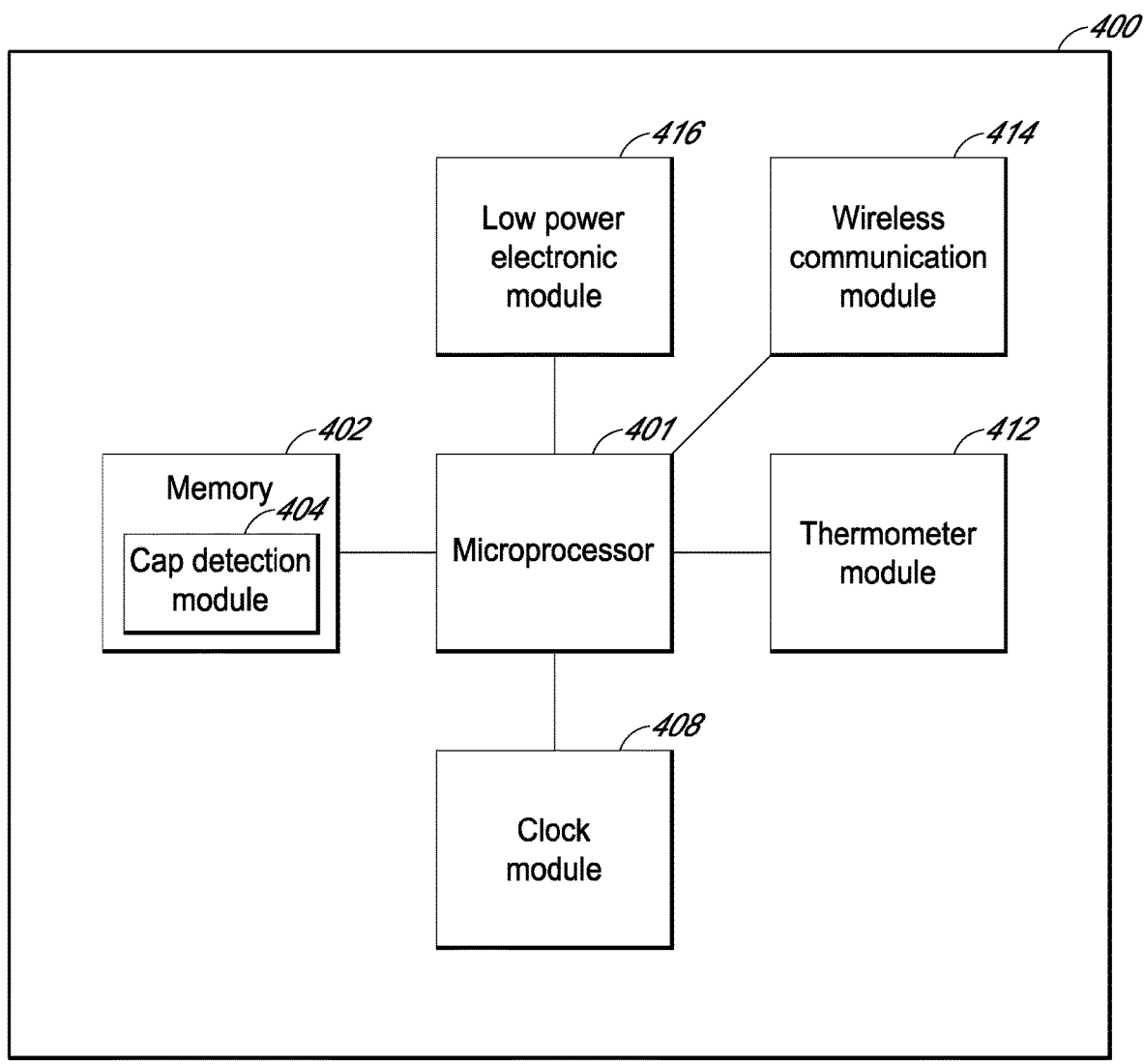
FIG. 4 depicts a block diagram of a dose monitoring device in accordance with an illustrative embodiment.

FIG. 4 depicts a block diagram of an embodiment of a control system 400 for monitoring, recording and/or processing one or more dosing events in accordance with an illustrative embodiment. The electronic module 202 of the dose monitoring device 102 may comprise various modules described in the system 400 shown in FIG. 4. The control system 400 may comprise a microprocessor 401, a memory 402, a cap detection module 404, a clock module 408, a temperature module 412, a wireless communication module 414 and a low power electronic module 416. Each of these separate modules may be connected to one another within the module 202 (FIG. 3).

The microprocessor 401 may be configured to monitor, record and/or process dose events or cap removal and replacement events. The microprocessor 401 may infer dose events based on a combination of passively captured "cap off" and "cap on" events and associated timestamps. Dosing events may be processed by instructions to determine the validity of the dosing events. The instructions may process dosing events and reject accidental triggers. In another embodiment, dosing events may be combined with other data known about the patient, such as expected dose schedule, glucose levels and time of day, and analyzed by an instruction to determine if the cap events occur in a manner consistent with the user dosing insulin or to facilitate better medication adherence with existing medication delivery instruments. The instructions may reside in a companion app on a smartphone, such as the smartphone 150 depicted in FIG. 1. The microprocessor 401 may be connected to the memory 402, cap detection module 404, clock module 408, temperature module 412, wireless communication module 414 and the low power electronic module 416. The microprocessor 401 may also be connected to a sensor such as the switch 219 comprising a switch plate 220 and a switch strip 222 depicted in FIGS. 2 and 3. The microprocessor 401 may also be connected to an indicator such as the indicator 120 depicted in FIG. 1.

The memory 402 is connected to the microprocessor 401 and configured to store data and instructions required for processing data. The data may be from the switch 219 comprising the switch plate 220 and the switch strip 222 depicted in FIGS. 2 and 3. In one embodiment, the memory 402 may be configured to retain data for a defined number of the most recent injections. In an alternative embodiment, the memory 402 may be configured to retain data for only the most recent recorded injection.

The cap detection module 404 may be part of the memory 402 and configured to receive and store data from the switch 219 (depicted in FIGS. 2 and 3) regarding the presence or absence of the distal end of the pen body 104 in the replacement cap 102 and instructions required for processing such data.

The clock module 408 may be connected to the microprocessor 401 and configured to record or timestamp dose events or cap removal and replacement events. The clock module 408 can be configured to record a time at each instance that the switch 219 obtains data so that each set of data has an associated time. In one embodiment, the clock module 408 may comprise a digital clock.

The temperature module 412 is connected to the microprocessor 401 and is configured to measure and record temperature. The temperature module 412 may record temperature at a predetermined time, during a predetermined time period or at the time of dose events or cap removal and replacement events.

In an illustrative embodiment, the wireless communication module 414 is connected to the microprocessor 401 and is configured to allow for connectivity between the replacement cap 102 (i.e., a dose monitoring device) and the smartphone 150 (i.e., an external device) depicted in FIG. 1. The dose monitoring device 102 may transmit data captured by the dose monitoring device 102 and/or information processed from such data using any number of communication protocols such as Bluetooth Low Energy to a smartphone app, network backend or other receiving devices. The transmitted data and information may be used to monitor or promote adherence to a medication regimen.

In another embodiment, the communication module 414 may communicate with the external device 150 such as a mobile device, computer, server or any other electronic external device that is known in the art. The external device 150 may include a communication module for receiving data from or sending data to the communication module 414. The external device 150 may also comprise a user interface for accessing and reading data on the external device 150. The external device 150 may further comprise a processor. The processor can be configured to perform on-board processing of data received from the dose monitoring device 102 using instructions to determine the time that an injection occurred. The external device 150 may further include a power module to provide power to the electronic components of the external device 150.

The low power electronic module 416 may be connected to the microprocessor 401 and configured to supply power to the electronic components of the replacement cap 102 such as the electronic module 202 as depicted in FIGS. 2 and 3 and modules shown in FIG. 4. The low power electronic module 416 can be used in different mechanical housings to optimize reliability when used with insulin pens from different manufacturers. The low power electronic module 416 may be rechargeable. The low power electronic module 416 may also include an external switch. In one embodiment, the dose monitoring device such as the replacement cap 102 can be configured so that the dose monitoring device is activated at any time that the low power electronic module 416 is supplying power to the dose monitoring device. In an alternative embodiment, the dose monitoring device can be activated when the dose monitoring device is coupled to the medication delivery instrument such as the insulin pen body 104.

Figure 5:
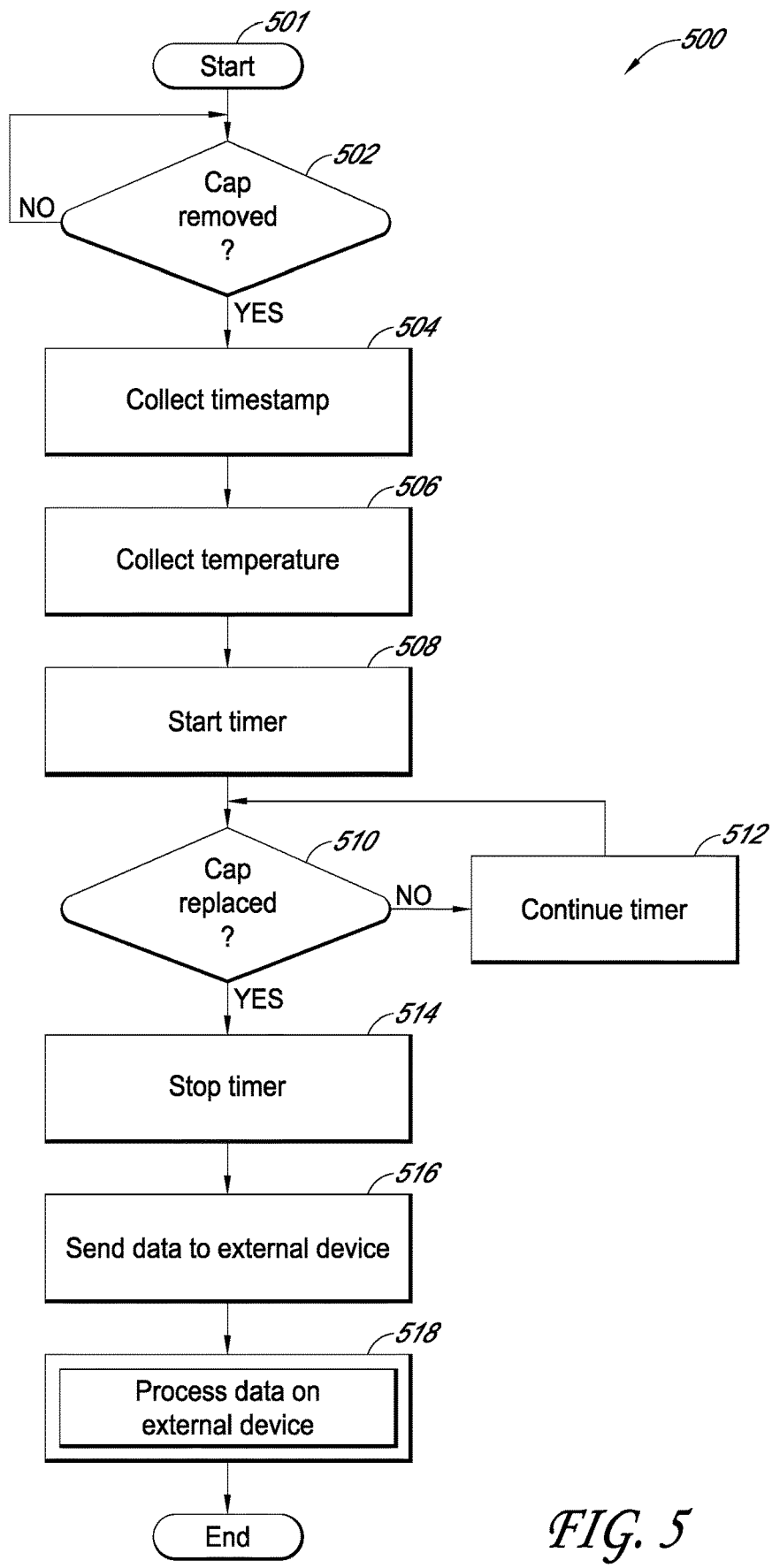
FIG. 5 depicts a flowchart of an embodiment of passively monitoring, recording and/or processing one or more dosing events in accordance with an illustrative embodiment.

FIG. 5 depicts a flowchart of a process 500 for passively monitoring, recording and/or processing one or more dosing events in accordance with an illustrative embodiment.

The process 500 begins at a start step 501, wherein a dose monitoring device, such as the replacement cap 102 depicted in FIG. 1, is engaged to a medication delivery instrument, such as the insulin pen body 104 depicted in FIG. 1. After the dose monitoring device is engaged to the medication delivery instrument, the process 500 moves to a decision step 502, wherein a decision is made whether the replacement cap 102 is removed from the insulin pen body 104. Either a sensor such as the switch 219 comprising a switch plate 220 and a switch strip 222 depicted in FIGS. 2 and 3 or an electronic module such as the cap detection module 404 depicted in FIG. 4 may make such a decision.

If a decision was made that the replacement cap 102 was not removed, the process 500 returns to the start step 501 and starts from the beginning. If the replacement cap 102 was removed from the insulin pen body 104, data starts to be monitored by one or more electronic modules as depicted in FIGS. 2, 3 and 4. The process 500 moves to a step 504 wherein a clock module 408 as depicted in FIG. 4 may collect timestamp data indicating when the replacement cap 102 is removed from the insulin pen body 104. The process 500 may also move to a step 506 to start collecting temperature and a step 508 to start a timer.

After the timer is started, the process 500 moves to a decision step 510, wherein a decision is made whether the replacement cap 102 is replaced onto the insulin pen body 104. If a decision is made at the decision step 510 that the replacement cap 102 is not replaced onto the pen body 104, the process 500 moves to a step 512 wherein the timer continues to run. The process 500 then returns to the decision step 510 to wait until the cap has been detected as having been replaced onto the pen body. If a decision is made at the decision step 510 that the replacement cap 102 is replaced onto the pen body 104, process 500 moves to a step 514 wherein the clock module 408 stops the timer. Then, the process 500 moves to a step 516, wherein data is transmitted to an external device for analysis. This transmission may be performed by a communication module, such as the communication module 414 depicted in FIG. 4.

After the data is transmitted to an external device, the process 500 moves to a process step 518, wherein the data is processed in the external device. The data detected and collected by the process 500 may be recorded in a memory of the external device. After the data is processed on the external device, the process 500 concludes at an end step.

In an illustrative embodiment, the data detected and collected by the process 500 may be recorded in a memory of the dose monitoring device, such as memory 402 depicted in FIG. 4. The data detected by the process 500 can also be displayed on a user interface, such as indicator 120 depicted in FIG. 1.

Figure 6:
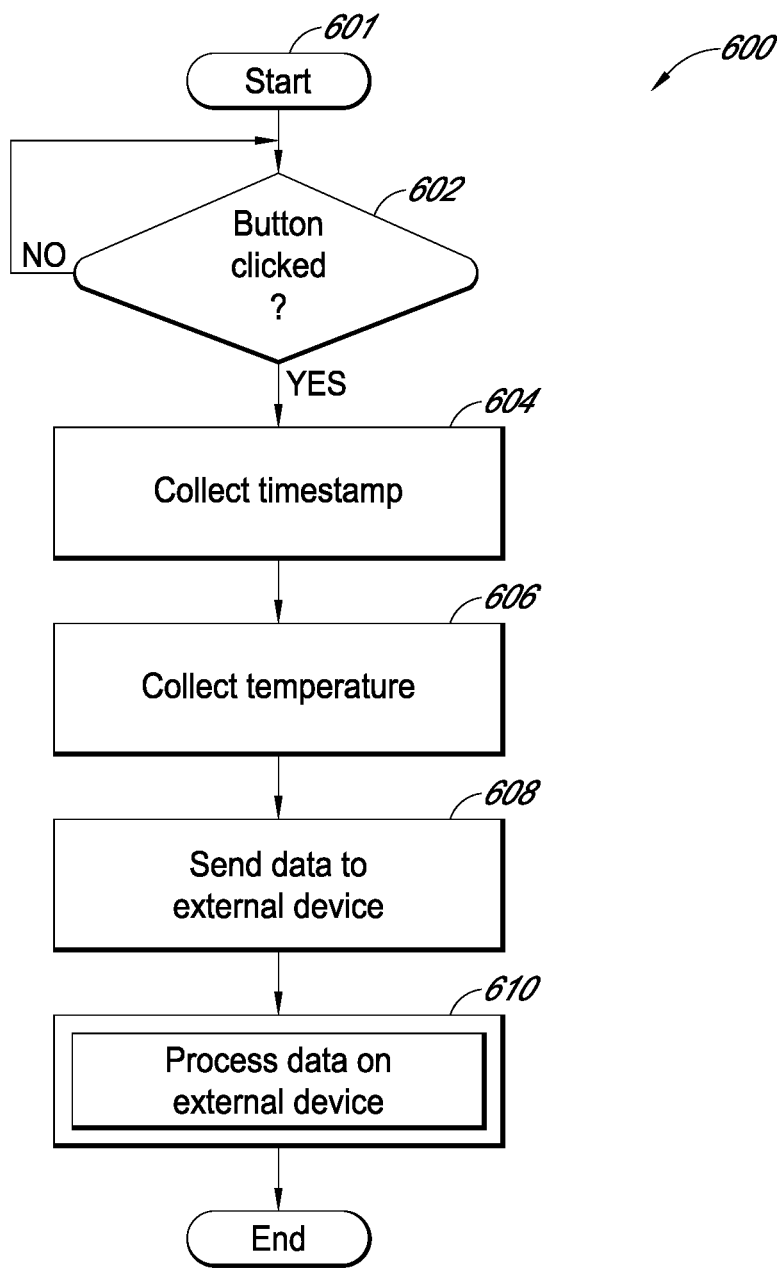
FIG. 6 depicts a flowchart of an embodiment of actively monitoring, recording and/or processing one or more dosing events in accordance with an illustrative embodiment.

FIG. 6 depicts a flowchart of a process 600 for an embodiment of actively monitoring, recording and/or processing one or more dosing events within a dose monitoring device, such as the pen cap 102.

The process 600 begins at a start step 601 and moves to a decision step 602, wherein a decision is made whether a button or other input on a dose monitoring device is clicked, pressed, or otherwise activated by the user. A sensor connected to the button may make such a decision. If a decision is made at the decision step 602 that the button or other input is not clicked or otherwise activated, the process 600 goes back to the start step 601 and starts from the beginning. If a decision is made at the decision step 602 that the button or other input is clicked or otherwise activated, data starts to be monitored by one or more electronic modules as depicted in FIGS. 2, 3 and 4. A clock module 408 as depicted in FIG. 4 may collect timestamp data indicating when the button is clicked or the input is activated (Step 604). A temperature module 412 as depicted in FIG. 4 may collect temperature data (Step 606). Then, the process 600 moves to a step 608, wherein data is transmitted from the dose monitoring device to an external device for analysis. This transmission may be performed by a communication module, such as the communication module 414 depicted in FIG. 4.

After the data is transmitted to an external device, the process 600 moves to a process step 610, wherein the data is processed in the external device. The data detected and collected by the process 600 may be recorded in a memory of the external device. After the data is processed on the external device, the process 600 concludes at an end step.

In an illustrative embodiment, the data detected and collected by the process 600 may be recorded in a memory of the dose monitoring device, such as memory 402 depicted in FIG. 4. The data detected by the process 600 can also be displayed on a user interface, such as indicator 120 depicted in FIG. 1.

Implementations disclosed herein provide systems, methods and apparatus for a module configured to couple with a medication delivery instrument. One skilled in the art will recognize that these embodiments may be implemented in hardware, software, firmware, or any combination thereof.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

Headings are included herein for reference and to aid in locating various sections. These headings are not intended to limit the scope of the concepts described with respect thereto. Such concepts may have applicability throughout the entire specification.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

The previous description of the disclosed implementations is provided to enable any person skilled in the art to make or use the embodiments described herein. Various modifications to these implementations will be readily apparent to those skilled in the art, and the generic principles defined herein may be applied to other implementations without departing from the spirit or scope of the embodiments described herein. Thus, aspects are not intended to be limited to the implementations shown herein but are to be accorded the widest scope consistent with the principles and novel features disclosed herein.

What is claimed is:

1. A dose monitoring device configured to couple with one or more injectable medication delivery instruments, comprising:
 a housing configured to mate with an injectable medication delivery instrument of the one or more injectable medication delivery instruments, the injectable medication delivery instrument comprising a body and a needle coupled to the body;
 one or more position sensors configured to detect removal of the dose monitoring device from the injectable medication delivery instrument and reinstallation of the dose monitoring device on the injectable medication delivery instrument and collect position sensor data;

one or more electronic modules configured to begin monitoring electronic module data when the one or more position sensors detect removal of the dose monitoring device from the injectable medication delivery instrument, wherein the electronic module data comprises timestamp data indicating a time at which the one or more position sensors detect the removal of the dose monitoring device from the injectable medication delivery instrument and timestamp data indicating a time at which the one or more position sensors detect the reinstallation of the dose monitoring device on the injectable medication delivery instrument, the one or more electronic modules comprising clock module configured to:

collect the timestamp data indicating the time at which the one or more position sensors detect the removal of the dose monitoring device from the injectable medication delivery instrument;

begin a timer when the one or more position sensors detect the removal of the dose monitoring device from the injectable medication delivery instrument;

stop the timer when the one or more position sensors detect reinstallation of the dose monitoring device on the injectable medication delivery instrument; and collect the timestamp data indicating the time at which the one or more position sensors detect the reinstallation of the dose monitoring device on the injectable medication delivery instrument; and a processor configured to determine a dose event based on the detected removal of the dose monitoring device from the injectable medication delivery instrument, the detected reinstallation of the dose monitoring device on the injectable medication delivery instrument, the timestamp indicating the time at which the one or more position sensors detect the removal of the dose monitoring device from the injectable medication delivery instrument, the timestamp indicating the time at which the one or more position sensors detect the reinstallation of the dose monitoring device on the injectable medication delivery instrument, and a time interval between beginning of the timer and stopping of the timer; and a communication module configured to transmit the position sensor data from the one or more position sensors to an external device.

2. The device of claim 1, wherein the injectable medication delivery instrument is an insulin pen.

3. The device of claim 2, wherein the dose monitoring device comprises a replacement cap configured to mate with the insulin pen.

4. The device of claim 1, wherein the one or more position sensors comprise a switch.

5. The device of claim 1, wherein the external device comprises a cellular telephone or a network server.

6. The device of claim 1, wherein the one or more electronic modules further comprise a temperature sensor configured to begin measuring ambient temperature when the one or more position sensors detect the removal of the dose monitoring device from the injectable medication delivery instrument.

7. The device of claim 1, further comprising one or more indicators configured to display the position sensor data.

8. The device of claim 1, further comprising a receiver module configured to receive information from the external device.

9. The device of claim 1, wherein the communication module is configured to transmit the position sensor data and the electronic module data to the external device after the one or more position sensors defect reinstallation of the dose monitoring device on the injectable medication delivery instrument.

10. A method for recording a dose event with a dose monitoring device, comprising:

providing an injectable medication delivery instrument comprising a body and a needle coupled to the body;

detecting a removal of the dose monitoring device from the injectable medication delivery instrument by one or more position sensors of the dose monitoring device, wherein the dose monitoring device comprises:

the one or more position sensors configured to collect position sensor data;

one or more electronic modules comprising a dock module configured to collect electronic module data, the one or more electronic modules comprising a dock module; and a transmitter for transmitting one or more of the position sensor data and the electronic module data to an external device;

beginning to monitor the electronic module data by the one or more electronic modules when the removal of the dose monitoring device from the injectable medication instrument is detected, wherein the electronic module data comprises timestamp data indicating a time at which the one or more position sensors detect the removal of the dose monitoring device from the injectable medication delivery instrument by the dock module and timestamp data indicating a time at which the one or more position sensors detect reinstallation of the dose monitoring device on the injectable medication delivery instrument by the dock module;

collecting the timestamp data indicating the time at which the one or more position sensors detect the removal of the dose monitoring device from the injectable medication delivery instrument by the clock module;

beginning a timer by the clock module when the removal of the dose monitoring device from the injectable medication instrument is detected;

detecting the reinstallation of the dose monitoring device on the injectable medication delivery instrument by the one or more position sensors;

stopping the timer by the dock module when the reinstallation of the dose monitoring device on the injectable medication instrument is detected;

collecting the timestamp data indicating the time at which the one or more position sensors detect the reinstallation of the dose monitoring device on the injectable medication delivery instrument by the dock module; and determining the dose event by a processor based on the detected removal of the dose monitoring device from the injectable medication delivery instrument, the detected reinstallation of the dose monitoring device on the injectable medication delivery instrument, the timestamp data indicating the time at which the one or more position sensors detect the removal of the dose monitoring device from the injectable medication delivery instrument, the timestamp data indicating the time at which the one or more position sensors detect the reinstallation of the dose monitoring device from the injectable medication delivery instrument, and a time interval between beginning of the timer and stopping of the timer.

11. The method of claim 10, wherein the one or more position sensors are configured to detect one or more additional dose events or one or more user interactions with the dose monitoring device or the injectable medication delivery instrument.

12. The method of claim 10, wherein the one or more position sensors comprise a switch.

13. The method of claim 10, wherein the injectable medication delivery instrument is an insulin pen.

14. The method of claim 13, wherein the dose monitoring device is a replacement cap.

15. The method of claim 10, further comprising displaying the position sensor data or the electronic module data on a user interface.

16. The method of claim 15, wherein the dose event is a resent dose event, wherein the method comprises displaying the electronic module date wherein the electronic module data comprises a timestamp indicating a time at which the one or more position sensors detect removal of the dose monitoring device from the injectable medication delivery instrument and a timestamp indicating a time at which the one or more position sensors detect reinstallation of the dose monitoring device on the injectable medication delivery instrument of one or more previous dose events.

17. The method of claim 10, further comprising transmitting the position sensor data and the electronic module data to the external device after the reinstallation of the dose monitoring device on the injectable medication delivery instrument is detected.

18. The method of claim 10, further comprising providing a second injectable medication delivery instrument; and
detecting engagement of the dose monitoring device with the second injectable medication delivery instrument.

19. The method of claim 10, further comprising analyzing the position sensor data and the electronic module data related to the dose event in combination with patient data to determine if the dose event is consistent with an insulin dose to a patient, the patient data comprising one or more of an expected dose schedule, a glucose level of the patient, and a time of day.

20. The method of claim 19, wherein the patient data comprises the expected dose schedule, the glucose level of the patient, and the time of day.

21. The method of claim 10, further comprising providing an alert to a user if a detection of the dose event does not occur at a predetermined time.

22. The method of claim 10, further comprising beginning to measure an ambient temperature by a temperature sensor when the removal of the dose monitoring device from the injectable medication instrument is detected.

* * * * *